US 6,607,535 B1

(12) United States Patent
Chan (10) Patent No.: US 6,607,535 B1
(45) Date of Patent: *Aug. 19, 2003

(54) UNIVERSAL BONE CEMENT PLUG AND METHOD OF USE

(76) Inventor: Kwan-Ho Chan, 4803 1st Pl., Lubbock, TX (US) 79410

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/244,644

(22) Filed: Feb. 4, 1999

(51) Int. Cl.[7] .................................................. A61F 2/28
(52) U.S. Cl. ............................................. 606/95; 606/92
(58) Field of Search ..................... 606/92–95; 206/557, 206/562, 564, 521.6, 521.7, 438, 363, 477, 570, 572, 364, 365; 623/16.11, 23.19, 23.2, 23.48; 215/251, 253, 298, 355; 4/295; 128/857, 858; 138/89, 90, 91; D24/106; 411/340

(56) References Cited

U.S. PATENT DOCUMENTS

| | | | | |
|---|---|---|---|---|
| 2,487,038 A | * | 11/1949 | Baum .......................... 128/857 |
| 3,490,083 A | * | 1/1970 | Firth ................................. 4/295 |
| 4,011,602 A | | 3/1977 | Rybicki et al. |
| 4,231,120 A | | 11/1980 | Day |
| 4,245,359 A | * | 1/1981 | Stuhmer ....................... 606/95 |
| 4,276,659 A | | 7/1981 | Hardinge |
| 4,293,962 A | | 10/1981 | Fuson |
| 4,302,855 A | | 12/1981 | Swanson |
| 4,324,331 A | * | 4/1982 | Ignasiak ....................... 206/363 |
| 4,344,190 A | | 8/1982 | Lee et al. |
| 4,447,915 A | | 5/1984 | Weber |
| 4,523,587 A | | 6/1985 | Frey |
| 4,627,434 A | | 12/1986 | Murray |
| 4,686,973 A | | 8/1987 | Frisch |
| 4,745,914 A | | 5/1988 | Frey et al. |
| 4,904,267 A | | 2/1990 | Bruce et al. |
| 4,936,859 A | | 6/1990 | Morscher et al. |
| 4,950,295 A | | 8/1990 | Weigum et al. |
| 4,967,584 A | | 11/1990 | Sato et al. |
| 4,994,085 A | | 2/1991 | Sawai et al. |
| 5,061,287 A | | 10/1991 | Feiler |
| 5,078,746 A | * | 1/1992 | Garner ......................... 606/95 |
| 5,092,891 A | | 3/1992 | Kummer et al. |
| 5,145,301 A | | 9/1992 | Yamamoto |
| 5,376,120 A | | 12/1994 | Sarver et al. |

(List continued on next page.)

FOREIGN PATENT DOCUMENTS

| | | |
|---|---|---|
| EP | 0006408 B1 | 1/1980 |
| GB | 2253564 A | 9/1992 |
| WO | WO 94/15544 A1 | 7/1994 |

OTHER PUBLICATIONS

Allo Pro AG of Switzerland, Polyethylene Medullary Plug According to Stuhmer/Weber, 1991.
Howmedica, Artisan™ Bone Plug, May 1996.
Ashok Samuel Paul and John Pattison Hodgkinson, "A New Femoral Cement Restrictor", The Journal of Arthroplasty vol. 7 Supplement, 1992, pp. 411–413.

*Primary Examiner*—Julian W. Woo
(74) *Attorney, Agent, or Firm*—Pandiscio & Pandiscio (57) ABSTRACT

A device and method for joint replacement surgery, such as total hip replacement surgery, including a bone cement plug which is adaptable to any size bone canal, an insertion tool for deploying the plug in the canal, and a cradle for storing the plug and insertion tool, The bone cement plug comprises a body defined by a series of separable units, each with a flange. The flanges decrease in diameter from the proximal end of the body to the distal end of the body. For smaller canals that cannot receive the large flanges, appropriate units of the plug may be removed, thus eliminating the oversized flanges in favor of the more appropriately sized flanges.

22 Claims, 6 Drawing Sheets

U.S. PATENT DOCUMENTS

| | | | | |
|---|---|---|---|---|
| 5,383,932 A | * | 1/1995 | Wilson et al. | 606/95 |
| 5,484,056 A | * | 1/1996 | Wood | 206/477 |
| 5,658,351 A | * | 8/1997 | Dudasik et al. | 606/95 |
| 5,662,657 A | | 9/1997 | Carn | |
| 5,766,178 A | * | 6/1998 | Michielli et al. | 606/95 |
| 5,772,031 A | * | 6/1998 | Landis | 206/438 |
| 5,782,917 A | * | 7/1998 | Carn | 606/95 |
| 5,879,403 A | * | 3/1999 | Ostiguy et al. | 623/23.48 |

* cited by examiner

UNIVERSAL BONE CEMENT PLUG AND METHOD OF USE

FIELD OF THE INVENTION

This invention relates to surgical devices and procedures in general. More particularly, this invention relates to bone cement plugs of the sort used in conjunction with bone cement dispensers to compact bone cement into bone canals during joint replacement surgeries.

BACKGROUND OF THE INVENTION

Bone cement plugs are well known in the art. Such devices are generally used in conjunction with bone cement dispensers to compact bone cement into a bone canal before fixing a prosthetic device in that bone canal. By way of example, bone cement plugs are commonly used in conjunction with bone cement dispensers to compact bone cement into the medullary canal of a femur before fixing the femoral stem of an artificial hip in that canal.

More particularly, in joint replacement surgeries, such as total hip and shoulder replacements, bone cement is commonly used to fix the stem of a prosthetic device in the medullary canal of a bone of the joint. In this respect, it has generally been found that a prosthetic device will be more securely fixed in a bone canal if the bone cement is well packed into the bone canal before the stem of the prosthetic device is positioned in the bone canal.

To this end, after initial preparation and cleaning of the bone canal, the distal portion of the canal is generally occluded with a bone cement plug. The bone cement plug limits uncontrolled flow of bone cement into the distal portion of the bone canal. Ideally, the bone cement plug limits the column of bone cement to about 1 to 2 cm beyond the distal tip of the stem of the prosthesis. After the bone cement plug has been set at the distal portion of the bone canal, bone cement is injected into the distal-most part of the occluded bone canal, adjacent to the plug, using a bone cement dispenser having a long nozzle. The bone canal is then filled with bone cement in a retrograde fashion, by withdrawing the nozzle of the bone cement dispenser from the distal end of the bone canal toward the proximal end of the bone canal as the cement issues from the nozzle. Retrograde filling helps to avoid trapping air in the distal-most part of the bone canal.

After the bone canal has been filled with bone cement, a bone canal pressurizer is connected to the bone cement dispenser. The pressurizer is pressed against the open end of the bone so as to occlude the proximal end of the bone canal. Then more cement is injected into the bone canal, through the pressurizer, under pressure. Under such pressurization, the cement in the bone canal intrudes into the interstices of the inner surface of the bone wall defining the bone canal. When the bone cement sets, a micro-interlock is established between the cement and the irregularities of the inner surface of the bone wall. This significantly enhances fixation of the prosthetic device in the bone canal.

A variety of bone cement plugs are known in the art.

See, for example, the bone cement plugs described and illustrated in U.S. Pat. Nos. 4,245,359; 4,276,659; 4,293,962; 4,302,855; 4,344,190; 4,447,915; 4,627,434; 4,686,973; 4,697,584; 4,745,914; 4,936,859; 4,950,295; 4,994,085; 5,061,287; 5,078,746; 5,092,891; 5,376,120; and 5,383,932.

See also, for example, the bone cement plug described and illustrated in British Patent Document No. 2,253,564A.

See also, for example, the publication entitled "Polyethylene medullary plug according to Stuhmer/Weber" distributed by ALLO PRO AG of Switzerland.

See also related apparatus described and illustrated in U.S. Pat. Nos. 4,011,602; 4,523,587; and 4,904,267.

See also related apparatus described and illustrated in European Patent Document No. 0,006,408 B1; and PCT Patent Document No. WO 94/15544.

Unfortunately, all of the bone cement plugs developed to date tend to suffer from one or more significant disadvantages. For example, in general, fixation of the bone cement plug depends on the friction established between the wall of the bone canal and the bone cement plug. Currently, the most common surgical technique is to first measure the size of the prepared bone canal. This typically involves sequentially inserting a number of different "sizers" into the bone canal so as to determine the gross cross-sectional diameter of the canal at the desired depth. Having thus determined the size of the bone canal, an over-sized plug is inserted into the canal so as to occlude the bone canal at the desired depth.

If the bone cement plug is not sufficiently over-sized relative to the diameter of the bone canal, or if the plug is too easily deformable, the engagement of the bone cement plug with the wall of the bone canal will be less than optimal, which may lead to complications. For example, during the aforementioned pressurization phase, or during the subsequent insertion of the prosthesis, increased pressure of the bone cement can cause the insufficiently-anchored plug to migrate distally.

On the other hand, if the bone cement plug is too greatly over-sized, and/or if the plug is overly rigid, the bone cement plug cannot be inserted into the bone canal to the desired depth. Also, excessively forceful insertion of the bone cement plug into the bone canal can cause the wall of the bone canal to fracture in some circumstances.

In the past, people have traditionally attempted to address these problems by providing plugs in a variety of different sizes for the surgeon to choose from. Unfortunately, this increases the cost of manufacturing the plugs and also increases the cost of inventory.

The foregoing demonstrates the need for a novel bone cement plug that may be adapted to fit any size bone canal. Ideally, a bone cement plug should be easy to deploy at the desired depth in the bone canal and effective in closing off that bone canal. The bone cement plug must also be bio-compatible with the patient. Furthermore, the bone cement plug should be inexpensive to produce.

SUMMARY OF THE INVENTION

These and other objects are addressed by the present invention, which comprises a novel device and method for use during joint replacement surgery, such as total hip replacement surgery. The present invention provides a universal bone cement plug which is appropriate for use in any size bone canal. The universal bone cement plug comprises a plurality of detachable units with flanges of decreasing diameter. The invention also provides an insertion tool for deploying the bone cement plug in a bone canal, and a cradle for storing the plug and insertion tool.

The bone cement plug is easy to deploy and align at a desired depth in a bone canal. The rigid, but deformable, plug occludes the bone canal and retains cement in the cavity so defined. The plug is bio-compatible with the patient.

A bone cement plug formed in accordance with the present invention includes a body defined by a series of separable units. Each unit has one or more flexible flanges. Preferably the flanges are slit at their periphery. The flanges decrease in size from the proximal end of the body to the distal end of the body. The largest flange accommodates the largest bone canal reasonably expected to be encountered during surgery. For smaller bone canals in which the largest flange would not fit, appropriate units of the plug may be removed, thus eliminating the oversized flanges in favor of the more appropriately sized flanges.

A first embodiment of the bone cement plug facilitates separating of the units by cutting the body, preferably with the aid of a notch or score line in the body.

A second embodiment of the bone cement plug facilitates separating of the units by tearing the body, preferably with the aid of a notch or score line in the body.

A third embodiment of the bone cement plug facilitates separating of the units by disengaging a fastening mechanism located between adjacent separable units.

Whether whole or truncated, the body of the bone cement plug presents an interface which is engageable by the insertion tool, such that the bone cement plug may be releasably attached to the insertion tool.

The insertion tool facilitates deploying the bone cement plug at a desired depth in the bone canal. An insertion tool formed in accordance with the present invention provides a handle for grasping by the surgeon, a shaft, and a distal end that releasably engages the slug.

The cradle stores the bone cement plug and the insertion tool prior to use. The cradle also provides firm support for the plug should a surgeon need to cut down the plug prior to deploying it in a bone canal. A cradle formed in accordance with the present invention includes a base with an anvil mounted thereon for receiving the plug. At least one set of fingers is preferably mounted on the base for retaining the insertion tool.

BRIEF DESCRIPTION OF THE DRAWINGS

These and other features of the present invention will be more fully disclosed or rendered obvious by the following detailed description of the invention, which is to be considered in conjunction with the accompanying drawings wherein like numbers refer to like parts and further wherein.

DETAILED DESCRIPTION OF THE INVENTION

Figure 1:
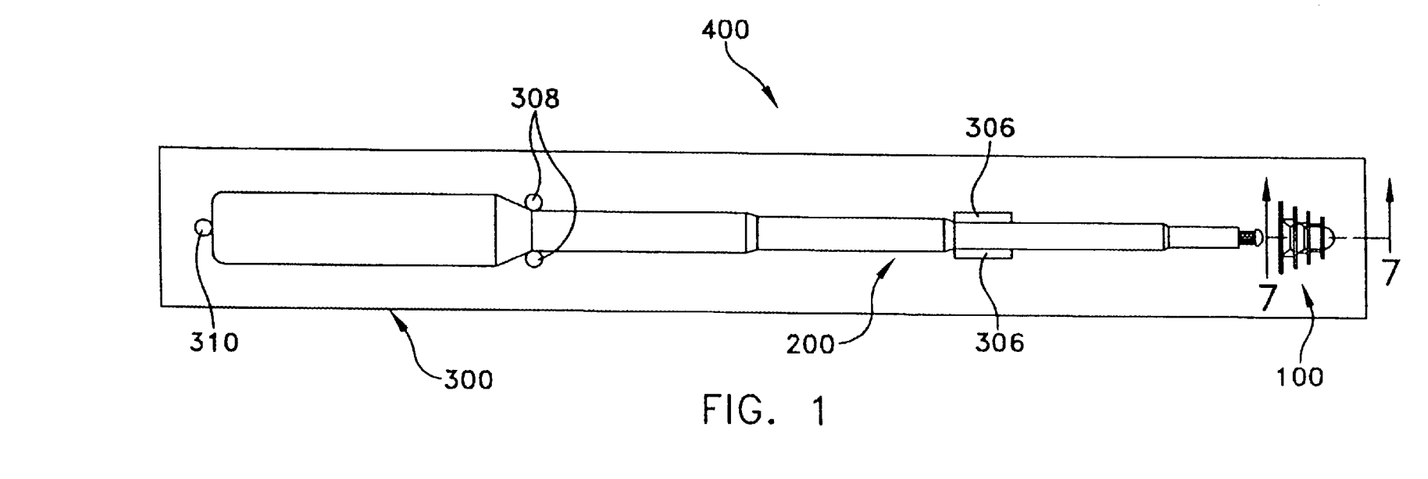
FIG. 1 is a top plan view of a bone cement plug, insertion tool and cradle, all formed in accordance with the present invention.
Figure 2:
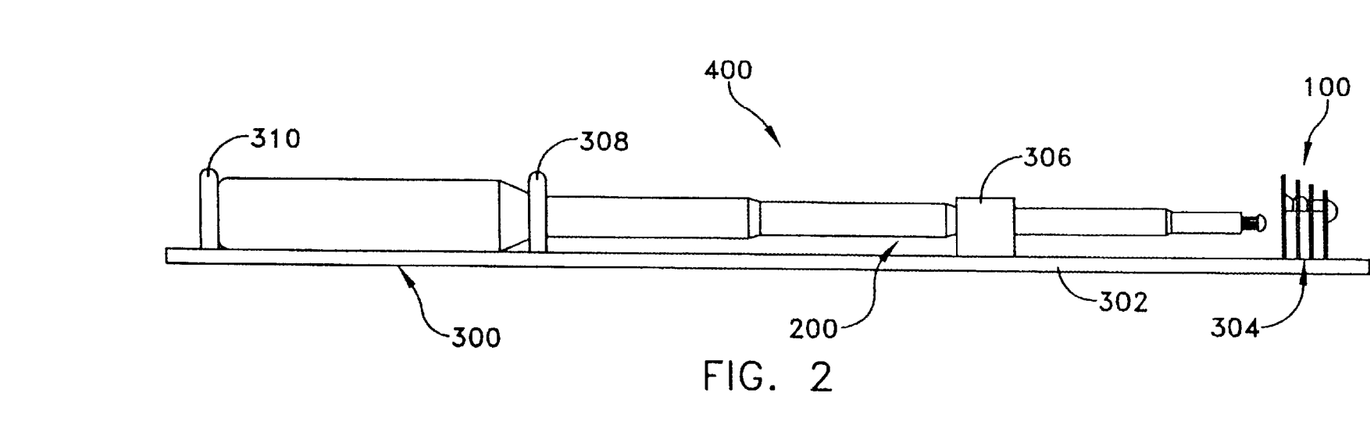
FIG. 2 is a side elevational view of the apparatus of FIG. 1.
Figure 3:
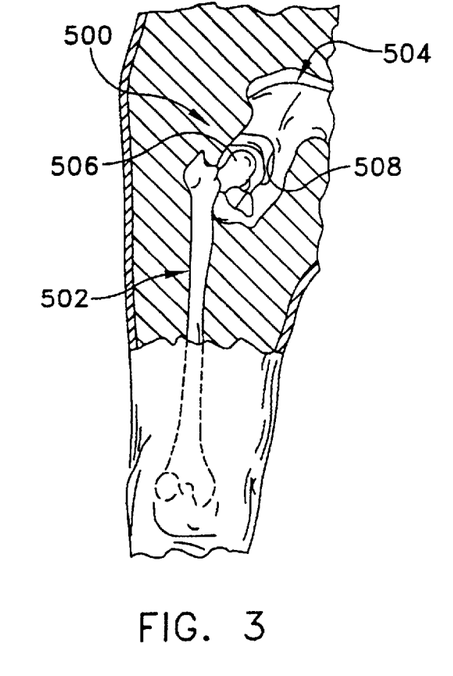
FIG. 3 is a partial cross-sectional view of a human hip joint.
Figure 4:
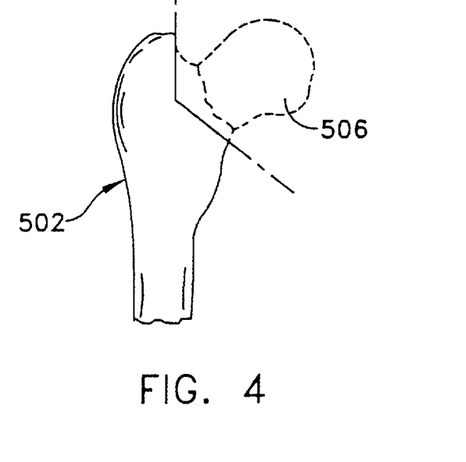
FIG. 4 is a partial front elevational view of a human femur, with a portion to be removed being shown in phantom.
Figure 5:
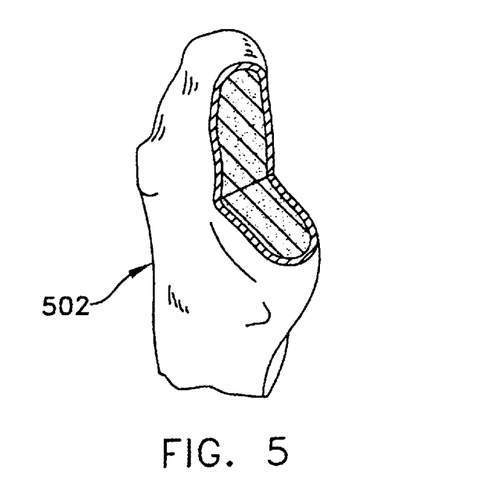
FIG. 5 is a partial perspective view of a human femur, with a portion removed.
Figure 6:
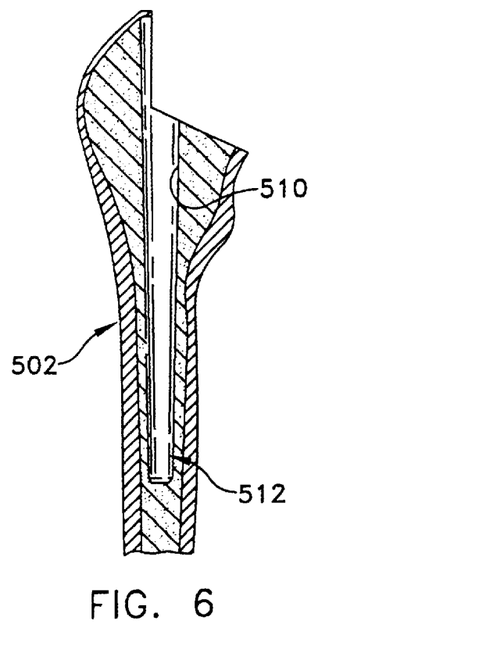
FIG. 6 is a partial cross-sectional view of a human femur, with a portion removed and with a broached medullary canal.

Referring first to FIGS. 1 and 2, the present invention provides a bone cement plug 100, an insertion tool 200 and a cradle 300, which together define an overall kit 400. In general, in use, the surgeon first determines what size bone cement plug should be used to occlude the subject bone canal. If necessary, the surgeon may modify the size of plug 100, e.g., by cutting it down. After any such re-sizing of the bone cement plug, the surgeon attaches the plug to insertion tool 200. With the insertion tool 200, the surgeon deploys plug 100 in the subject bone canal so that the plug becomes lodged in the canal. The insertion tool 200 is then disengaged from plug 100 and removed. The occluded portion of the bone canal is then filled with bone cement and fitted with a prosthesis.

More particularly, and referring now to FIGS. 3–6, a human hip joint 500 is shown. The hip joint 500 includes a femur 502 and a pelvis 504. Femur 502 has a head 506. Head 506 is received in a socket 508 of pelvis 504. When head 506 and socket 508 do not function properly, such as in the case where a patient suffers from serious joint deterioration, head 506 and/or socket 508 may be replaced. Where head 506 is to be replaced, head 506 of femur 502 is exposed and removed. Once head 506 is removed, a medullary canal 510 is broached into femur 502. Prior to introducing cement into medullary canal 510, a bone cement plug 100 is introduced into the canal and positioned in the distal end 512 thereof. The bone cement plug 100 must be sized to fit securely in canal 510 and occlude the canal.

A surgeon ascertains the size of the distal end 512 of bone canal 510 by introducing any number of sizing tools (not shown) into canal 510. After the surgeon has ascertained the size of the distal end 512 of canal 510, the surgeon must determine an appropriate size for the bone cement plug which is to occlude the canal 510. Prior to the present invention, the surgeon would typically have to select one particular bone plug from a number of different bone cement plugs, each having different sizes. The present invention eliminates this situation, by providing a universal bone cement plug which can be properly sized by the surgeon for any size bone canal.

Figure 7:
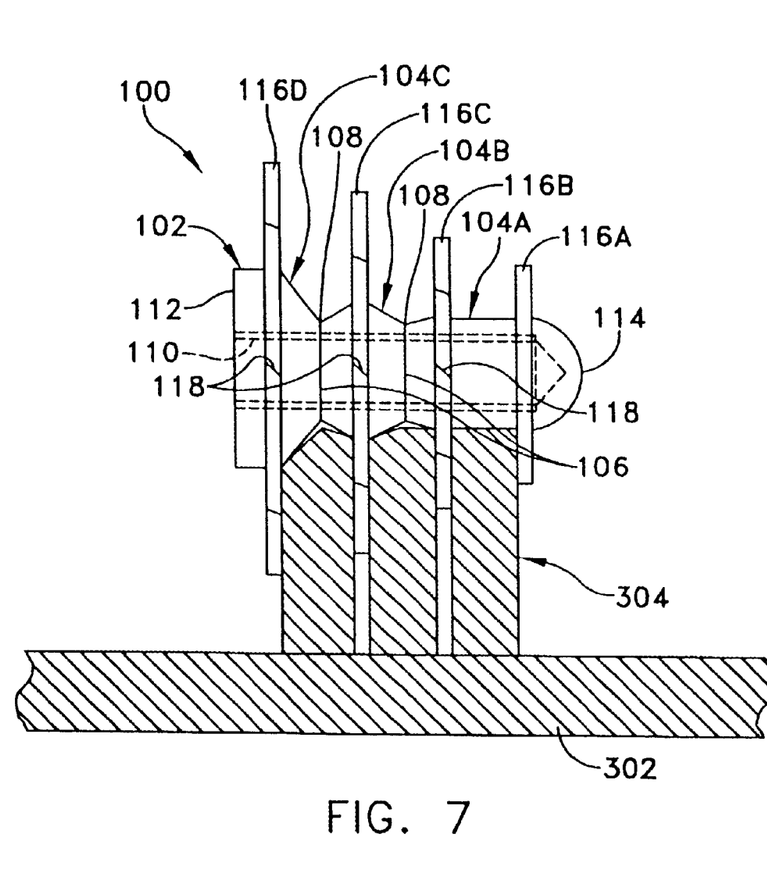
FIG. 7 is an enlarged, partial cross-sectional view taken along line 7—7 of FIG. 1.
Figure 8:
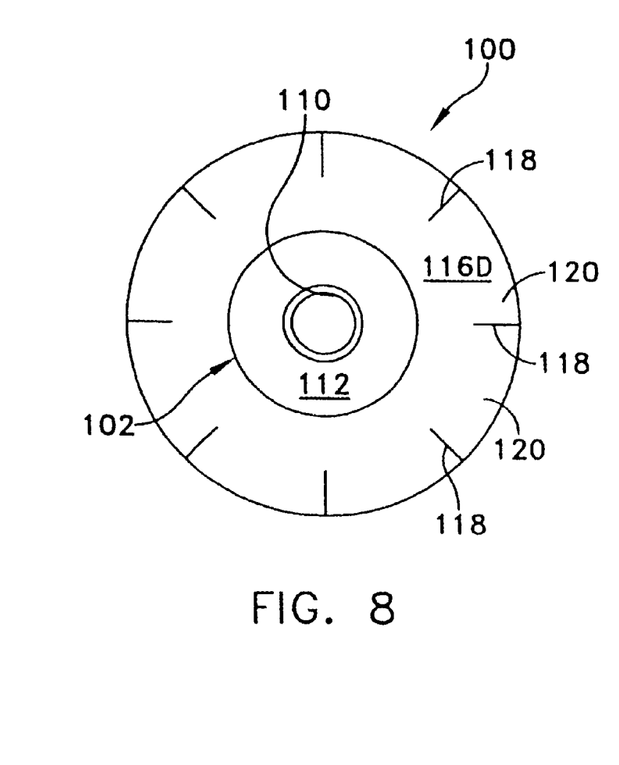
FIG. 8 is an end view showing the proximal end of the bone cement plug shown in FIG. 7.

Referring next to FIGS. 7 and 8, bone cement plug 100 is shown in greater detail. Bone cement plug 100 comprises a singular, substantially rigid body 102.

Body 102 consists of a plurality of different segments or units 104, i.e., 104A, 104B, 104C, etc. A particular unit 104 may be separated from the remaining units 104 by severing the body 102 along a surface 106 between the units 104, e.g., with a knife or scalpel. Body 102 also may be torn or broken so as to separate the units 104 from one another. To facilitate separation, body 102 may also include necked-down regions 108, or score lines (not shown), which may be aligned with surfaces 106. The invention also may rely on other mechanisms for introducing local material weakness at desired locations along the body 102, such as a notch (not shown), so as to facilitate separating one unit 104 from another unit 104.

Figure 9:
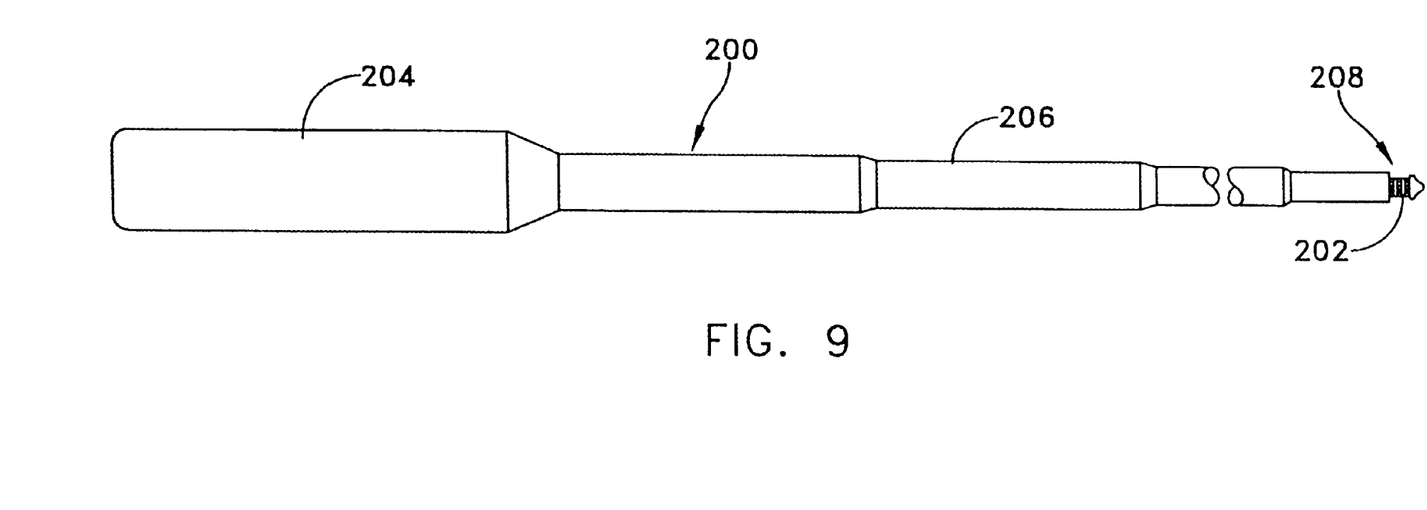
FIG. 9 is an enlarged side elevational view of the insertion tool shown in FIGS. 1 and 2.

Body 102 is releasably engageable with insertion tool 200 (FIG. 9). This is so regardless of whether one or more of the units 104 have been removed from body 102. To that end, body 102 may employ any satisfactory fastening mechanism for connecting bone cement plug 100 to insertion tool 200. With the embodiment shown in FIGS. 1, 2, 7 and 8, body 102 is shown as having female threads 110 extending from the proximal end 112 toward the distal end 114 thereof. The removal of a unit 104 does not detrimentally impact the fastening mechanism (in this case, the threads 110) or the orientation thereof relative to body 102. Regardless of how many units 104 are removed from body 102, the threads 110 remain engageable by the insertion tool. For this embodiment, the insertion tool 200 has male threads 202 (FIG. 9) that are engageable with the female threads 110 of body 102, as discussed in more detail below.

Figure 10:
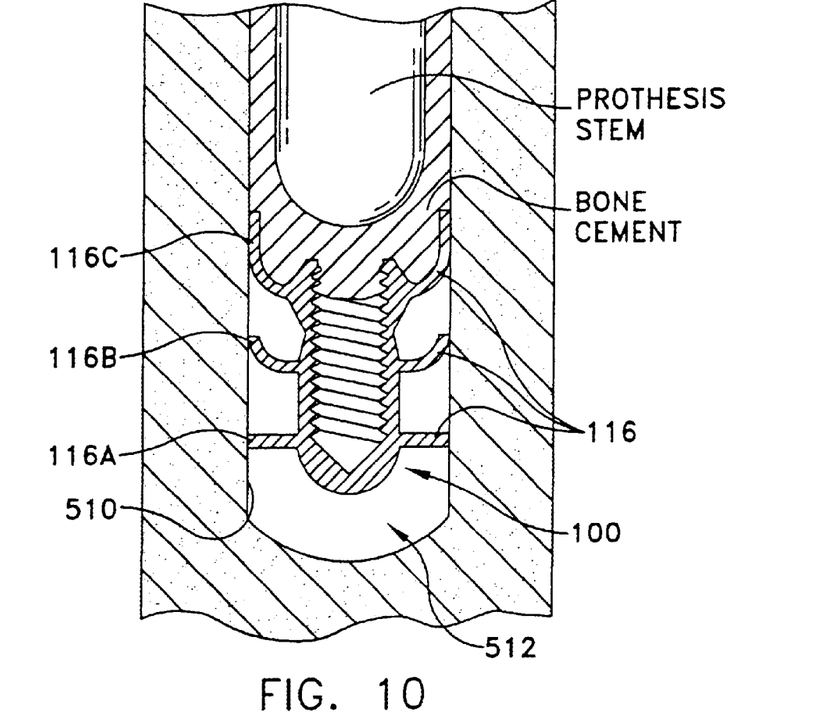
FIG. 10 is a partial side elevational view, partially in section, of a bone cement plug formed in accordance with the present invention, with the plug being shown deployed in the medullary canal of a bone.
Figure 11:
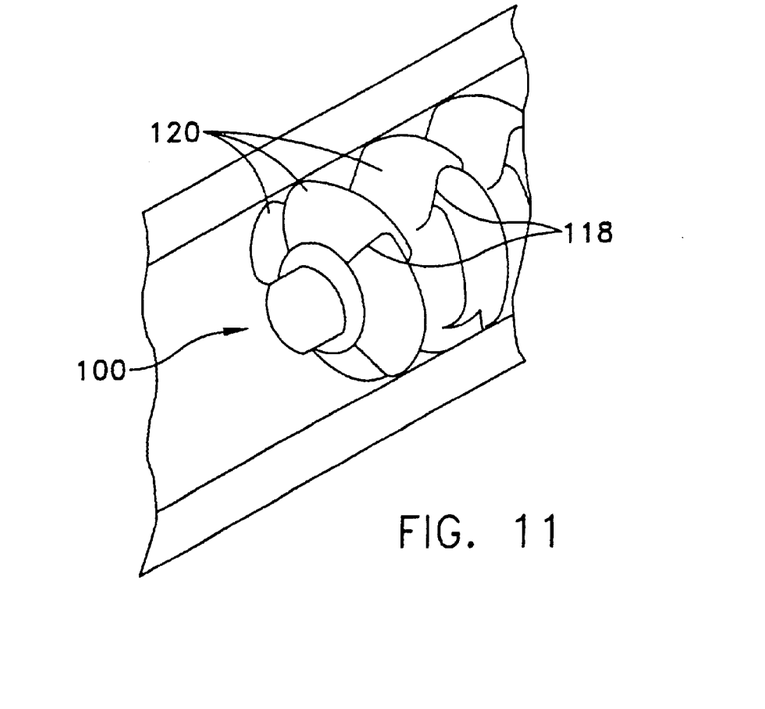
FIG. 11 is a schematic perspective view of a portion of the structure shown in FIG. 10.

Referring again to FIG. 7, each unit 104 has at least one flexible flange 116. As shown in FIG. 8, the flanges 116 preferably include slits 118 which define flaps 120 therebetween. Although shown extending radially in FIG. 8, the slits 116 may extend along any direction which permits the flaps 120 to overlap one another when bone cement plug 100 is deployed in a bone canal. Furthermore, as seen in FIG. 7, slits 118 are preferably angled relative to the longitudinal axis of the bone cement plug. This angulation helps flaps 120 slide over one another when the bone cement plug is deployed in a bone canal and the flanges 120 are compressed radially. In addition, such angulation also provides sharp edges which can catch on the side wall of the bone canal, so as to help stabilize the plug as the insertion tool 200 is unthreaded from the deployed bone cement plug. Referring now to FIGS. 10 and 11, it will be seen that as the cross-sectional area in which a plug 100 is positioned decreases, the flanges 116 bend. Often, when a slit-less flange is forced to bend, the generally radial surface buckles and causes gaps to occur along the periphery of a flange 116. This is especially true when symmetrical flanges mate with irregularly-shaped cross sections, such as when a generally round flange mates with a typically oval-shaped medullary canal. As seen in FIG. 11, because flanges 116 are provided with the slits 118, the flaps 120 may overlap one another so as to provide a good seal with the walls of the bone canal.

Referring again to FIG. 7, the present plug 100 is shown with multiple flanges 116. Multiple flanges allow seating of the plug 100 so that it resists movement and tilting relative to the bone, especially under torsional stresses. As shown in FIGS. 10 and 11, the larger flanges 116C and 116B are positioned so that they bend and wedge into place in the medullary canal 510. The smaller flange 116A may, but does not have to, be wedged into place and bent against the sides of the medullary canal 510. In some cases, the smaller flange 116A may not even touch the sides of medullary canal 510. In any case, the smaller flange 116A generally pilots the plug 100 through the typically tapering medullary canal 510 and keeps the plug 100 centered and aligned therein.

The size of a medullary canal varies greatly from patient to patient. Accordingly, no one size flange, or set of flanges, is appropriate for all canals. The present bone cement plug 100 is adaptable to any size canal because the body 102 of plug 100 is defined by multiple, detachable units 104. In the case where one or more flanges 116 are too large for a particular medullary canal 510, the unit or units 104 from which an inappropriately large flange or flanges 116 extend may be separated from the remainder of body 102, leaving one or more unit or units 104 having smaller flanges 116. For example, referring to FIG. 7, if flange 116D is too large for insertion in a medullary canal 510, the unit 104C is detached from the remaining units 104B and 104A, which remain attached to one another.

Referring again to FIGS. 1, 2 and 9, insertion tool 200 has a handle 204 which a surgeon grips. Tool 200 also has a shaft 206 which extends from handle 204 to a distal end 208. The distal end 208 of tool 200 is configured so as to be releasably engageable with the proximal end of any unit of the body 102. For example, as shown, the distal end 208 of insertion tool 200 may have male threads 202 thereon that mate with the female threads 110 of the plug body 102. It will be appreciated that this threaded connection between bone cement plug 100 and insertion tool 200 will permit the plug and insertion tool to be quickly and easily attached together prior to deployment of the plug in a bone canal; and once the plug has been lodged in the distal end of the bone canal, whereby the plug will be prevented from rotating within the bone canal, the threaded connection will permit plug 100 and insertion tool 200 to be quickly and easily detached from one another so as to leave plug 100 deployed within the bone canal.

The present invention also provides a cradle 300 (FIG. 2) including a base 302. An anvil 304 (FIGS. 2 and 7) is mounted on the base 302. The anvil 304 is configured to receive a bone cement plug 100. Additionally, the anvil 304 holds the plug 100 securely so that a surgeon may inspect, size or otherwise prepare the plug 100 for use. For example, in the event that a unit 104 of the plug 100 must be removed so as to achieve a better fit in a medullary canal, and in the event that a cutting tool is to be used to separate a unit 104 from the body 102 of the plug, the anvil 304 maintains the plug 100 in position so that it does not move during cutting, and provides an excellent cutting surface for the cutting tool to contact. At least one set of fingers 306 (FIG. 2) is mounted on the base 302 for retaining the insertion tool 200 in a lateral direction. A second set of fingers 308 (FIG. 2) may also be mounted on the base 302 for retaining the insertion tool 200 in a lateral and axial direction. Additionally, a stop 310 (FIG. 2) may be mounted on the base 302 for retaining the insertion tool 200 in an axial direction.

Figure 12:
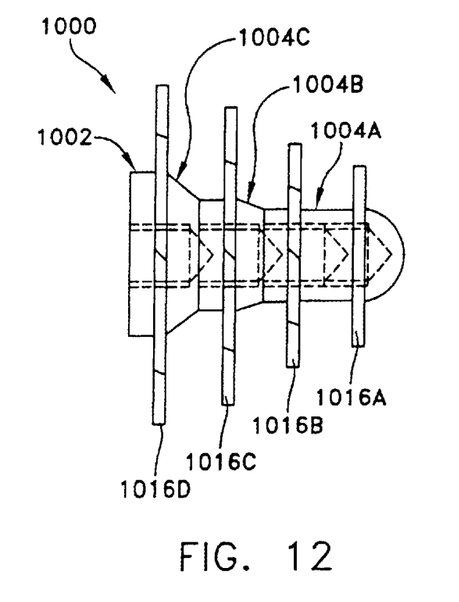
FIG. 12 is a side elevational view of an alternative form of bone cement plug formed in accordance with the present invention.
Figure 13:
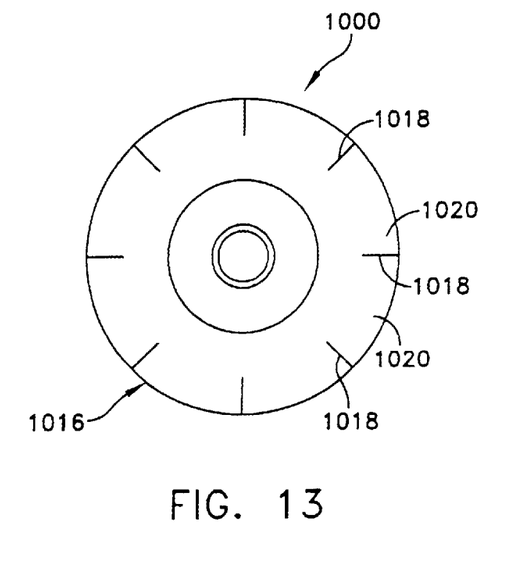
FIG. 13 is an end view showing the proximal end of the bone cement plug shown in FIG. 12.
Figure 14:
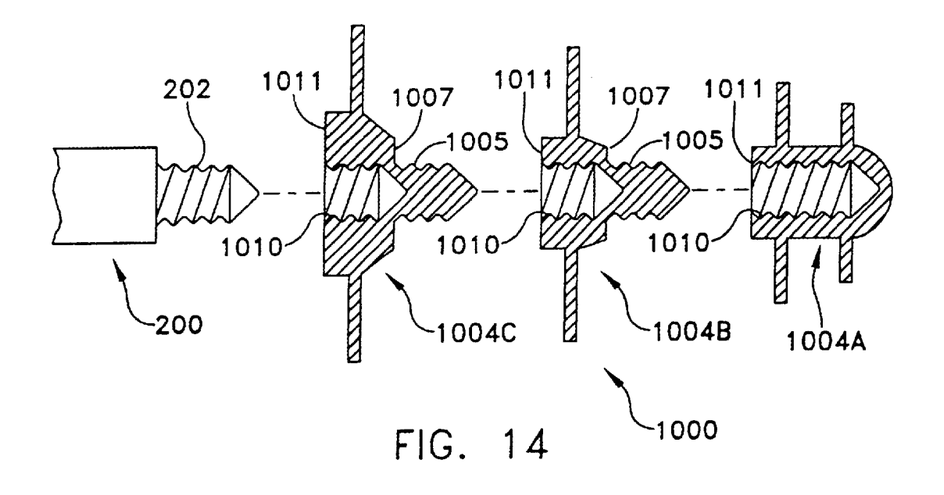
FIG. 14 is a side elevational view, in section, of the bone cement plug of FIG. 12, with the plug's separable units being shown in exploded view, and adjacent to the distal end of the insertion tool.

Referring next to FIGS. 12–14, there is shown a bone cement plug 1000 which is also formed in accordance with the present invention. Bone cement plug 1000 is similar to the aforementioned bone cement plug 100, except that the body 1002 of bone cement plug 1000 is formed from a plurality of separate, interengageable units 1004, i.e., 1004A, 1004B, 1004C, etc. Units 1004 together form a substantially rigid body 1002. Any fastening convention that permits the units 1004 to releasably interengage one another, and insertion tool 200, may be used. For example, other than the distal-most unit 1004A, the units 1004 may have male threads 1005 formed on a distal end 1007 thereof; and all of the units 1004 may have female threads 1010 formed in the proximal ends 1011 thereof. When assembled to define a body 1002, for example, male threads 1005 of unit 1004C threadingly engage female threads 1010 of unit 1004B. Female threads 1010 of the proximal-most unit 1004 are engaged by the male threads 202 of insertion tool 200.

Each unit 1004 also has at least one flexible flange 1016. As shown in FIG. 13, the flanges 1016 preferably have slits 1018 which define flaps 1020 therebetween.

In one preferred method of use, bone cement plug 1000 is packaged in kit 400 in its fully assembled state, i.e., with all of the units 1004 connected together so as to form the complete body 1002, and with bone cement plug 1000 received by the cradle's anvil 304. Thereafter, during use, the surgeon removes bone cement plug 1000 from anvil 304, re-sizes it if necessary by removing one or more units 1004, and then mounts the remaining assembly to insertion tool 200 for insertion in a bone canal.

In yet another method of use, a bone cement plug 100, or a fully assembled bone cement plug 1000, is sterilely packaged in a disposable kit 400, which also includes a disposable insertion tool 200 made of injection molded plastic. Alternately, the bone cement plug 100, or the bone cement plug 1000, can be packaged sterilely, with or without the anvil. In this latter case, the surgeon is provided with a resterilizable insertion tool 200 at the time of surgery.

Bone cement plug 100 and bone cement plug 1000 are formed out of a bio-compatible material. In one form of the invention, they are formed out of a non-absorbable plastic material such as polyethylene. In another form of the invention, they are formed out of a biodegradable material of the sort well known in the art.

The invention provides many features. One feature is that the present bone cement plug is universal and adaptable for any size medullary canal. Since only one universal plug needs to be provided, the cost of manufacturing and of inventory is lower than with conventional plugs. Another feature is that, regardless of how the plug is sized, it is engageable with the insertion tool so that the plug may be deployed in a medullary canal. A further feature is the cradle for storing the plug and insertion tool, which also provides an anvil for modifying the size of the plug. An additional feature is that the present bone cement plug is easy to deploy and align at a desired depth in a medullary canal. Yet another feature of the present invention is that the rigid, but deformable, plug occludes a medullary canal and retains bone cement in the occluded cavity prior to insertion of a prosthetic appliance. Yet a further feature of the invention is that the plug is bio-compatible with the patient.

The present invention is not limited to the foregoing specific embodiments, but also encompasses all improvements and substitutions within the scope of the appended claims.

What is claimed is:

1. A bone cement plug comprising a body adapted to be sized and defined by at least two units, each of said aty least two units being sized for placement into the medullary canal of a bone, each of said at least two units including at least one flange being substantially planar and extending substantially perpendicularly to a longitudinal axis of said body, and one of said at least two units being detachable from another one of said at least two units, and two of said at least two units having a necked-down region therebetween for cutting therethrough.

2. The plug of claim 1, wherein said body has a notch between two of said at least two units.

3. The plug of claim 1, two of said at least two units being releasably interengageable.

4. The plug of claim 1, said at least two units being releasably engageable with an insertion tool.

5. The plug of claim 4, wherein said at least two units have female threads and the insertion tool has male threads, said female threads and said male threads being releasably interengageable.

6. The plug of claim 1, wherein each said at least one flange has at least one slit.

7. The plug of claim 6, wherein said at least one slit is angled relative to the longitudinal axis of the plug.

8. The plug of claim 1, wherein said plug is formed out of a biodegradable material.

9. The plug of claim 1, wherein said plug is formed out of polyethylene.

10. A bone cement plug comprising a body adapted to be sized and defined by at least two units, each of said at least two units being sized for placement into the medullary canal of a bone, each of said at least two units including at least one flange being substantially planar and extending substantially perpendicularly to a longitudinal axis of said body, and one of said at least two units being detachable from another one of said at least two units, and said one of said at least two units having female threads and said another of said at least two units having male threads, said female threads and said male threads being releasably interchangeable.

11. A kit for occluding a bone canal comprising:
   a plug comprising a body defined by at least two units, each of said at least two units including at least one flange and being substantially planar and extending substantially perpendicularly to a longitudinal axis of said body, and one of said at least two units being detachable from another one of said at least two units, said one of said at least two units having female threads and said another of said at least two units having male threads, said female and said male threads being releasably interchangeable.

12. The kit of claim 11, including an insertion tool releasably engageable with said plug.

13. The kit of claim 12, said cradle being adapted to receive said insertion tool.

14. The kit of claim 11, said cradle including an anvil for supporting said plug during operations thereon to prepare said plug for use.

15. A method for occluding a bone canal comprising:
   providing a plug sized for placement into the medullary canal of a bone and adapted to be sized, said plug comprising a body defined by at least two units, each of said at least two units including at least one flange being substantially planar and extending substantially perpendicularly to a longitudinal axis of said body, and one of said at least two units being detachable from another one of said at least two units, and two of said at least two units having a necked-down region therebetween for cutting therethrough;
   ascertaining a cross-sectional diameter of a target portion of the canal which is to receive the plug; and
   modifying the size of the plug, prior to insertion in the bone canal, to fit in the target portion by cutting through said necked-down region.

16. The method of claim 15, including deploying the plug in the canal.

17. The method of claim 16, wherein deploying the plug is accomplished with an insertion tool which is releasably engageable with said plug.

18. The method of claim 15, wherein modifying the size of the plug is accomplished with a cradle adapter to receive and support the plug during said modifying.

19. A bone cement plug comprising a body defined by at least two units, each of said at least two units being sized for placement into the medullary canal of a bone, each of said at least two units including at least one flange being substantially planar and extending substantially perpendicularly to a longitudinal axis of said body, and one of said at least two units being detachable from another one of said at least two units, wherein each said at least one flange has at least one slit.

20. A bone cement plug comprising a body defined by at least two units, each of said at least two units being sized for placement into the medullary canal of a bone, each of said at least two units including at least one flange being substantially planar and extending substantially perpendicularly to a longitudinal axis of said body, and one of said at least two units being detachable from another one of said at least two units, wherein each said at least one flange has at least one slit and said at least one slit is angled relative to the longitudinal axis of said body.

21. A kit for occluding a bone canal comprising:

a plug comprising a body defined by at least two units, each of said at least two units being sized for placement into the medullary canal of a bone, each of said at least two units including at least one flange being substantially planar and extending substantially perpendicularly to a longitudinal axis of said body, and one of said at least two units being detachable from another one of said units, and two of said at least two units having a necked-down region therebetween for cutting therethrough; and a cradle adapted to receive said plug and including an anvil for supporting said plug during operations thereon to prepare said plug for use.

22. A method for occluding a bone canal comprising:

providing a plug sized for placement into the medullary canal of a bone and adapted to be sized, said plug comprising a necked-down region for cutting therethrough;

ascertaining a cross-sectional diameter of a target portion of the canal which is to receive the plug; and modifying the size of the plug, prior to insertion in the bone canal, to fit in the target portion, wherein modifying the size of the plug is accomplished by cutting through said necked-down region with a cradle adapted to receive and support the plug during said sizing.

* * * * *